United States Patent [19]

Maurer et al.

[11] Patent Number: 5,046,511

[45] Date of Patent: Sep. 10, 1991

[54] VAGINAL ELECTRODE WITH SNAP-ON ELECTRODE PAD AND METHOD FOR PREPARING ELECTRODE FOR USE

[75] Inventors: Donald D. Maurer; Stacy D. Mattson, both of Anoka, Minn.

[73] Assignee: Empi, Inc., St. Paul, Minn.

[21] Appl. No.: 442,248

[22] Filed: Nov. 28, 1989

[51] Int. Cl.$^5$ .......................... A61N 1/05; A61N 1/18
[52] U.S. Cl. ..................... 128/788; 128/798
[58] Field of Search ............... 128/788, 784, 642, 783, 128/798, 639, 641

[56] References Cited

U.S. PATENT DOCUMENTS

| | | | |
|---|---|---|---|
| 1,740,240 | 12/1929 | Honey | 128/788 |
| 4,094,309 | 6/1978 | Grzenia | 128/2.1 |
| 4,248,247 | 2/1981 | Ware et al. | 128/798 |
| 4,296,760 | 10/1981 | Carlsson et al. | 128/788 |
| 4,476,872 | 10/1984 | Perlin | 128/642 |
| 4,635,641 | 1/1987 | Hoffman | 128/639 |
| 4,688,575 | 8/1987 | DuVall | 128/422 |
| 4,770,168 | 9/1988 | Kaali et al. | 128/788 |
| 4,781,196 | 11/1988 | Killion | 128/642 |
| 4,785,828 | 11/1988 | Maurer | 128/788 |

Primary Examiner—William E. Kamm
Assistant Examiner—Kevin Pontius
Attorney, Agent, or Firm—Kinney & Lange

[57] ABSTRACT

A vaginal electrode including a carrier and electrode pad is adapted to be inserted into a woman's vagina to stimulate and constrict muscles therein and prevent the unwanted flow of urine through the urethra. The carrier includes a tubular member having a circular cross-section with a plurality of sets of conductive first snap fastener sections arranged circumferentially about and communicating with its exterior surface. The pad is removably secured to the carrier by a plurality of sets of conductive second snap fastener sections which are releasably cooperable with the first snap fastener sections of the carrier. The pad has a plurality of electrically isolated electrode sections, each section in electrical contact with one of the sets of second snap fastener sections, to contact the vagina. The carrier includes leads to couple electrical energy to the set of first snap fastener sections.

37 Claims, 2 Drawing Sheets

VAGINAL ELECTRODE WITH SNAP-ON ELECTRODE PAD AND METHOD FOR PREPARING ELECTRODE FOR USE

BACKGROUND OF THE INVENTION

1. Field of the Invention

The present invention relates generally to the field of electrical neuromuscular stimulation for controlling urinary incontinence in women. In particular, the present invention is a two-piece vaginal electrode having a carrier and snap-on electrode pad.

2. Description of the Prior Art

Electrical neuromuscular stimulation, whereby motor nerve fibers are electrically stimulated by means of transcutaneously applied pulses of electrical current to cause contraction of muscles the fibers innervate, is widely used to assist persons afflicted with motor dysfunctions in performing muscle contraction maneuvers. This technique is also used to re-educate patients in the proper use of the dysfunctional muscles.

For example, in cases in which urinary incontinence in women is caused by the patient's inability to properly contract the external sphincter of the urethra, it has been shown that neuromuscular stimulation of the dysfunctional muscles by means of a vaginal or anal electrode can effectively prevent the unwanted flow of urine. Furthermore, through the use of such an electrode some patients can educate themselves to voluntarily or automatically impede the flow of urine.

Electrical stimulators for controlling urinary incontinence generally include a vaginal plug with one or more electrodes in the form of conductive metal rings. When the plug is inserted, electrodes contact the vaginal wall. A cable extends from the plug to a controller or stimulator which generates the stimulation signals. The controller is typically worn externally, attached to clothing.

There is a continuing need for improved vaginal electrodes which can be used to prevent the unwanted flow of urine. In addition to being effective, the electrodes must be convenient to use. The device must therefore be easy to insert and extract. To ensure proper hygiene, the stimulator should be capable of being easily cleaned. To be commercially viable, the electrode must be relatively inexpensive to manufacture.

SUMMARY OF THE INVENTION

The present invention is a vaginal electrode adapted to be inserted into a woman's vagina to stimulate and constrict the muscles therein and prevent the flow of urine through the urethra. The vaginal electrode includes an electrode pad which is removably mounted to a carrier prior to insertion into the vagina. The carrier includes an elongated member having at least two first conductive fastener sections mounted on and communicating with an exterior surface of the elongated member. Leads for coupling electrical energy are attached to the conductive fastener sections.

The electrode pad includes a flexible pad member having a vaginal contact surface and a carrier contact surface. The vaginal contact surface includes at least two electrically isolated electrode sections. At least two second conductive fastener sections which communicate with the carrier contact surface are mounted to the pad in electrical contact with the electrode sections. The second conductive fastener sections are cooperable with the first fastener sections to removably secure the electrode pad to the carrier and couple electrical energy to the electrode sections.

In a preferred embodiment, the elongated member includes a plastic tubular member having a circular cross-section and a plurality of apertures therethrough. A plurality of sets of first conductive snap fastener sections are arranged circumferentially about the elongated member with a conductive metal strip coupling the snap fastener sections of each set. The second fastener sections are second snap fastener sections. The electrode sections of the pad are conductive polymer strips arranged on the vaginal contact surface so as to be positioned adjacent the sets of first snap fastener sections when the electrode pad is snapped onto the carrier.

The vaginal stimulator of the present invention is convenient and easy to use. Before each use, a new electrode pad is fastened to the carrier. The vaginal electrode affords a high degree of hygiene as the electrode pad is inexpensive and may be used once and subsequently disposed. The electrode carrier can be washed and reused.

BRIEF DESCRIPTION OF THE INVENTION

DETAILED DESCRIPTION OF THE PREFERRED EMBODIMENTS

Figure 1:
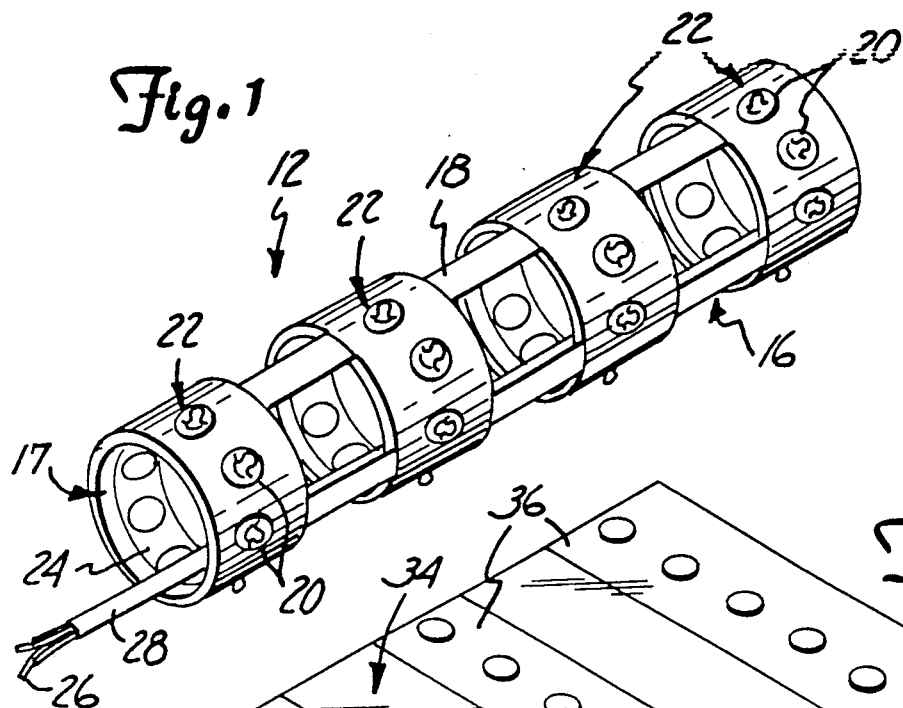
FIG. 1 is a perspective view of a carrier of a vaginal electrode in accordance with the present invention.

The present invention is a two-piece vaginal electrode for controlling urinary incontinence in women. When inserted into the vagina and coupled to a controller, the electrode applies a train of electric pulses to tissues and causes the contraction of the external sphincter and other pelvic floor musculature. The urethra is thereby constricted, preventing the unwanted flow of urine. The electrode is relatively inexpensive to manufacture and simple to use. It also offers a high degree of hygiene.

A vaginal electrode 10 in accordance with the present invention can be described with reference to FIGS. 1-4. As shown, vaginal electrode 10 includes a carrier 12 and an electrode pad 14. Electrode pad 14 is removably wrapped around and secured to the carrier 12 before electrode 10 is inserted into a woman's vagina. Carrier 12 includes an elongated tubular member 16, preferably formed of relatively stiff plastic material. In the embodiment shown, carrier 12 has a circular cross-section, a hollow center defining an interior surface 17, and an exterior surface 18 with a plurality of apertures therethrough. Sets 22 of conductive first snap fastener sections 20 are mounted to and arranged circumferentially about the tubular member 16 and in communication with exterior surface 18.

Snap fastener sections 20 of each set 22 are electrically interconnected by conductive members such as 24 which traverse the interior surface 17 of the elongated member 16. Preferably, conductive members 24 are metal strips which are coated with a fluid resistant polymer. Each conductive member 24 is connected to an individual lead 26 of an electrode cable 28. Leads 26 couple electrical stimulation signals to the first snap fastener sets 22. The housing of cable 28 can be formed of plastic material and is attached to the interior surface 17 of tubular member 16.

In the embodiment shown, the apertures within the tubular member 16 are arranged circumferentially about the tubular member between adjacent first snap fastener sets 22. The apertures allow carrier 12 to be lightweight, while maintaining the strength and durability of the elongated member 16.

Figure 2:
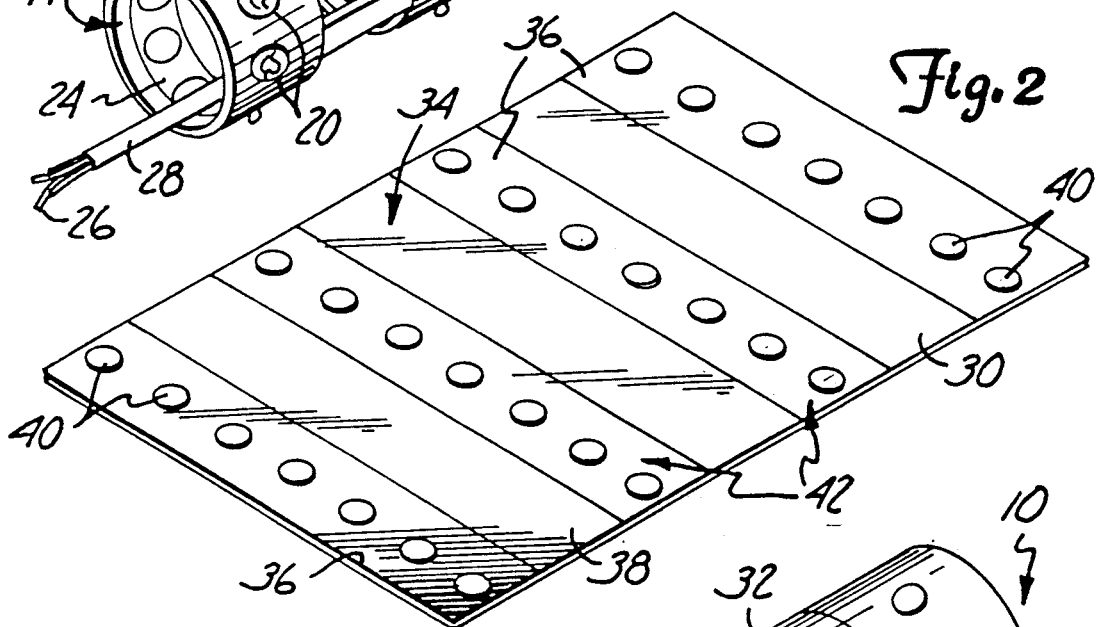
FIG. 2 is a perspective view of a pad member prior to assembly onto the carrier shown in FIG. 1.

FIG. 2 illustrates the electrode pad 14 when it is removed from the carrier 12. The electrode pad 14 includes a flexible pad member 30 which is conformable to the elongated member 16 of carrier 12. The flexible pad member 30 includes a vaginal contact surface 32 and a carrier contact surface 34. A plurality of electrically isolated electrode sections 36 are arranged on the vaginal contact surface 32 so as to be positioned adjacent the snap fastener sets 22 of the tubular member 16 when the electrode pad 14 is wrapped around the carrier 12. The electrode sections 36 can be formed of conductive polymer strips which are electrically isolated from one another by nonconductive polymer strips 38.

A plurality of second snap fastener sections 40 are mounted to electrode pad 14 in communication with the carrier contact surface 34. Second snap fastener sections 40 are releasably cooperable with snap fastener sections 20, and are arranged about the electrode pad 14 to form second snap fastener sets 42. The second snap fastener sets 42 correspond positionally to the first snap fastener sets 22 such that the first and second fastener sections align when the electrode pad 14 is wrapped around the carrier 12. Electrode pad 14 can therefore be releasably snapped onto carrier 12. The first snap fastener sections 20 couple electrical stimulation signals from controller 29 to the second snap fastener sections 40 and electrode sections 36.

Figure 3:
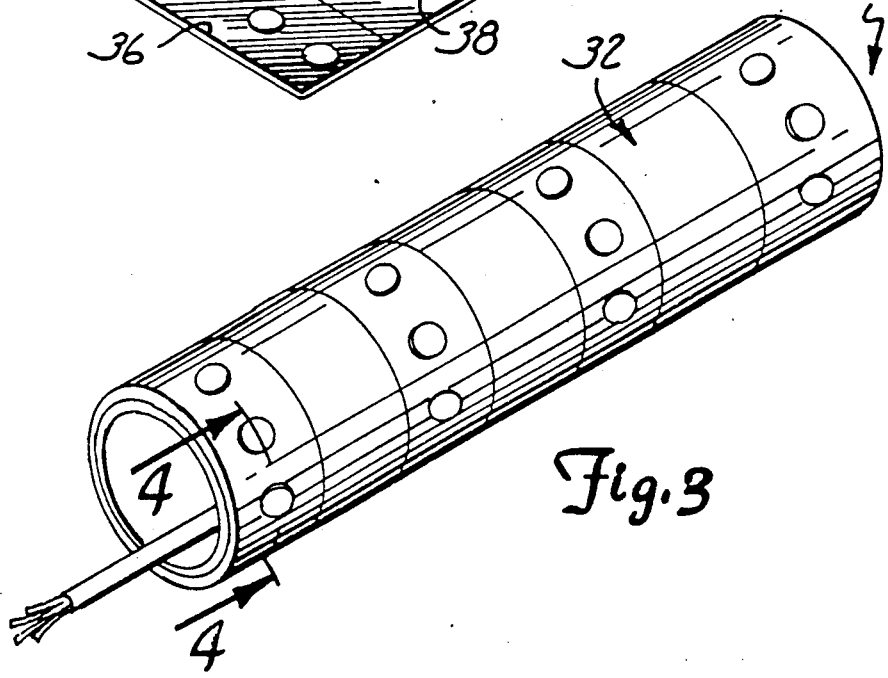
FIG. 3 is a perspective view illustrating the vaginal electrode in its assembled form.
Figures 4, 5:
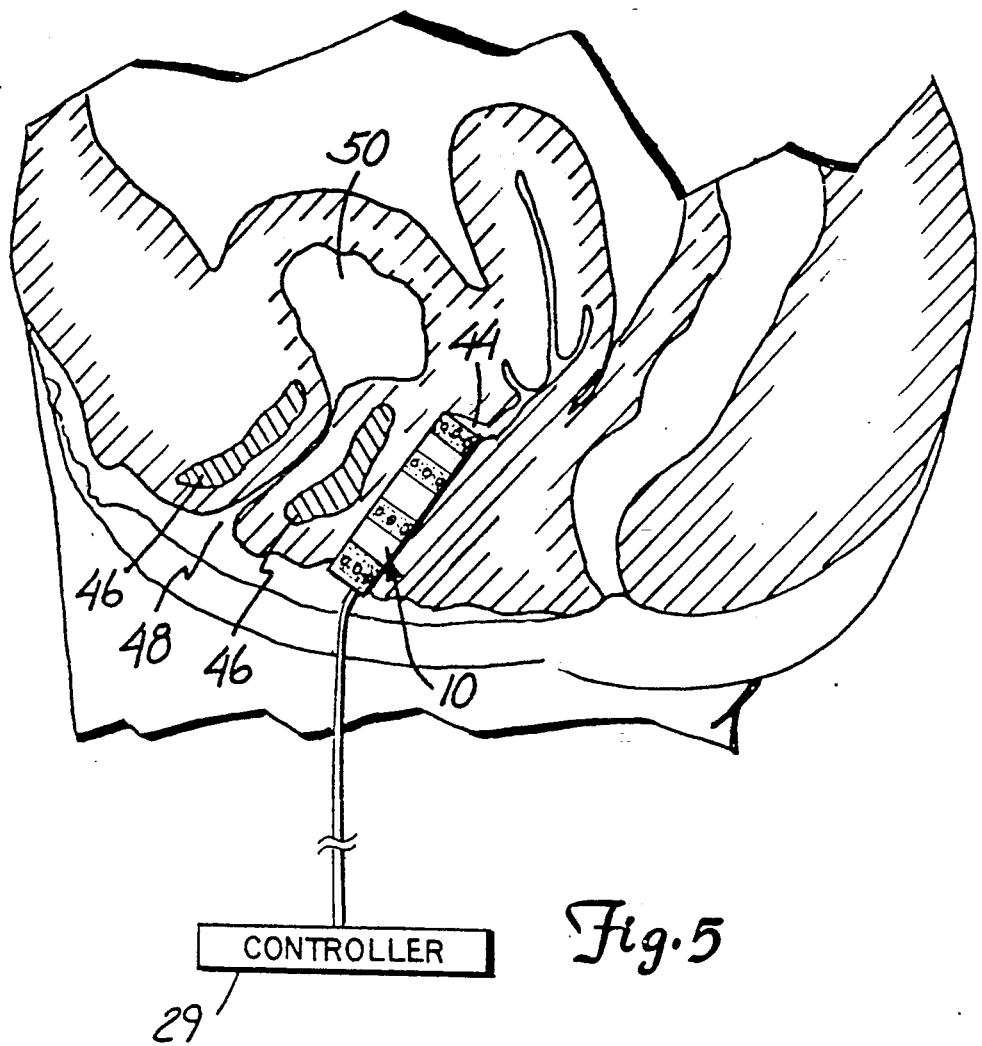
FIG. 4 is a cross-sectional view taken on the line 3—3 of FIG. 3.
FIG. 5 is a cross-sectional view showing the vaginal electrode operatively positioned in the vagina of a user.

Vaginal electrode 10 is shown in its assembled form in FIG. 3. To assemble the vaginal electrode, the second snap fastener sections 40 of the electrode pad 14 are aligned and pressed into the first snap fastener sections 20 of the carrier 12. The electrode pad 14 completely encircles the carrier 12. Once assembled, the vaginal electrode 10 can be inserted into a women's vagina 44 as shown in FIG. 5. The vaginal electrode is positioned such that an end through which electrode cable 28 protrudes fits even with the introitus of vagina 44. The electrode sections 36 of vaginal electrode 10 will then be in physical contact with tissues surrounding various muscles 46, including the external sphincter muscle, within the woman's pelvic region.

Once the vaginal electrode 10 is properly positioned within vagina 44, controller 29 (which is typically clipped to the clothing of the user) is manipulated by an operator to provide stimulating signals to electrode sections 36. The stimulation signals can be applied through one or more pairs of electrode sections 36 to most effectively recruit muscles 46. Electrode sections 36 transcutaneously transmit the stimulation signals to the woman's pelvic region so as to cause contraction of the various muscles 46, thereby constricting the urethra 48 and preventing the flow of urine from the woman's bladder 50. Repeated use of the vaginal electrode 10 can retrain the various muscles surrounding the vagina 44 to automatically constrict and impede the flow of urine.

The vaginal electrode of the present invention provides a simple and hygienic method of controlling urinary incontinence. Prior to each use, a new pad is placed over the carrier. After removing the vaginal electrode from the vagina, the pad can be removed from the carrier and disposed. The carrier can then be washed to prepare it for a subsequent use.

Although the present invention has been described with reference to preferred embodiments, workers skilled in the art will recognize that changes may be made in form and detail without departing from the spirit and scope of the invention.

What is claimed is:

1. A vaginal electrode, including:
   a carrier for insertion into a vagina, comprising;
      an elongated member having an exterior surface;
      at least two first conductive fastener sections mounted to the elongated member and communicating with the exterior surface, each first conductive fastener section including a plurality of fasteners arranged in a ring around the elongated member; and
      leads for coupling electrical energy to the first conductive fastener sections; and
   an electrode pad removably mounted to the carrier, including:
      a generally rectangular flexible pad member conformable to the elongated member by wrapping around the elongated member so that a vaginal contact surface is facing outward and a carrier contact surface is facing inward, and so that first and second side edges are adjacent one another;
      at least two electrically isolated electrode sections on the vaginal contact surface of the pad member; and
      at least two second conductive fastener sections, each mounted to the pad in electrical contact with one of the electrode sections and communicating with the carrier contact surface, each of the second conductive fastener sections including a plurality of fasteners arranged in a band and cooperable with the fasteners of the first fastener sections to removably secure the electrode pad to the carrier and couple electrical energy to the electrode sections.

2. The vaginal electrode of claim 1 wherein the elongated member includes a tubular member having a generally circular cross sections and an interior surface.

3. The vaginal electrode of claim 2 wherein the carrier further includes:
   a conductive member coupling the fasteners of each section.

4. The vaginal electrode of claim 3 and further including a fluid resistant polymer coating over the conductive members.

5. The vaginal electrode of claim 1 wherein the elongated tubular member includes a plurality of apertures therethrough.

6. The vaginal electrode of claim 5 wherein the apertures are arranged circumferentially around the elongated tubular member and between adjacent sets of first conductive fastener sections.

7. The vaginal electrode of claim 5 wherein the elongated tubular member includes a plastic tubular member.

8. The vaginal electrode of claim 1 wherein each of the first and second conductive fastener sections is formed by a plurality of snap fasteners.

9. The vaginal electrode of claim 1 wherein the electrically isolated electrode sections of the pad member are arranged on the vaginal contact surface so as to be positioned adjacent the first conductive fastener sections when the electrode pad is mounted to the carrier.

10. The vaginal electrode of claim 1 wherein the electrode sections include conductive polymer sections.

11. The vaginal electrode of claim 10 and further including nonconductive polymer sections between the electrode sections.

12. A vaginal electrode, including:
a carrier for insertion into a vagina, comprising:
an elongated tubular member having a generally circular cross section and an exterior surface, the tubular member having a length and an outer circumference;
a plurality of sets of conductive first snap fastener sections mounted to and arranged about the tubular member and communicating with the exterior surface; and
leads for coupling electrical energy to the sets of first snap fastener sections; and
an electrode pad removably wrapped around and secured to the carrier; comprising:
a flexible pad member conformable to the elongated tubular member and having a vaginal contact surface and a carrier contact surface, the flexible pad member being generally rectangular with first and second side edges and first and second end edges, a length approximately equal to the length of the tubular member, and a width approximately equal to the circumference of the tubular member so that the first and second side edges are adjacent one another when the pad member is wrapped around the tubular member;
a plurality of electrode sections arranged on the vaginal contact surface of the pad member so as to be positioned adjacent the sets of first snap fastener sections when the pad member is wrapped around the carrier; and
a plurality of sets of conductive second snap fastener sections releasably cooperable with the first snap fastener sections, the fastener sections of each set in electrical contact with one of the electrode sections and communicating with the carrier contact surface to removably secure the electrode pad to the carrier and couple electrical energy to the electrode sections.

13. The vaginal electrode of claim 12 wherein the elongated tubular member includes a plastic tubular member.

14. The vaginal electrode of claim 12 and including a conductive member coupling the first snap fastener sections of each set of conductive first snap fastener sections.

15. The vaginal electrode of claim 14 and further including a fluid resistant polymer coating over the conductive members.

16. The vaginal electrode of claim 12 wherein the sets of conductive first snap fastener sections are arranged circumferentially around the elongated tubular member.

17. The vaginal electrode of claim 12 wherein the elongated tubular member includes a plurality of apertures therethrough.

18. The vaginal electrode of claim 17 wherein the apertures are arranged circumferentially around the elongated tubular member and between adjacent sets of conductive first snap fastener sections.

19. The vaginal electrode of claim 12 wherein the electrically isolated electrode sections of the pad member are arranged on the vaginal contact surface so as to be positioned adjacent the sets of first snap fastener sections when the pad member is wrapped around the carrier.

20. The vaginal electrode of claim 19 wherein the electrode sections of the pad member include conductive polymer strips.

21. The vaginal electrode of claim 20 and further including nonconductive polymer sections between the electrode sections.

22. A vaginal electrode pad configured to be removably wrapped around and secured to a generally cylindrical vaginal electrode carrier having first conductive fastener sections, including:
a flat, generally rectangular flexible pad member having first and second side edges and first and second side ends, the pad member being sufficiently flexible to wrap around and conform to the electrode carrier so that the first and second side edges are adjacent one another, and the pad member having a vaginal contact surface and carrier contact surface;
at least two electrically isolated electrode sections on the vaginal contact surface of the pad member, the electrode sections extending as generally parallel bands between the first and second side edges; and
at least two second conductive fastener sections, each mounted to the pad in electrical contact with one of the electrode sections and communicating with the carrie contact surface, the conductive fastener sections cooperable with the first conductive fastener sections to removably secure the electrode pad to the carrier and couple electrical energy to the electrode sections.

23. The vaginal electrode pad of claim 22 wherein the isolated electrode sections of the pad member include conductive polymer strips.

24. The vaginal electrode of claim 23 and further including nonconductive polymer strips separating the conductive polymer strips.

25. A vaginal electrode pad that can be removably wrapped around and secured to sets of conductive first snap fastener sections mounted in parallel bands to a vaginal electrode carrier, including:
a flexible pad member having a vaginal contact surface and a carrier contact surface the pad member having first and second side edges and first and second ends, the pad member being sufficiently flexible to wrap around the carrier so that the first and second side edges are adjacent one another;
a plurality of electrode sections arranged on the vaginal contact surface of the pad member so as to be positioned adjacent the sets of first snap fastener sections when the pad member is wrapped around the carrier, the electrode selections being generally parallel bands extending between the first and second side edges; and
a plurality of sets of conductive second snap fastener sections releasably cooperable with the first snap fastener sections, the fastener sections of each set in electrical contact with one of the electrode sections and communicating with the carrier contact surface to removably secure the electrode pad to the carrier and couple electrical energy to the electrode sections.

26. The vaginal electrode of claim 25 wherein the electrically isolated electrode sections of the pad member are arranged on the vaginal contact surface so as to be positioned adjacent the sets of first snap fastener sections when the pad member is wrapped around the carrier.

27. The vaginal electrode pad of claim 26 wherein the isolated electrode sections of the pad member include conductive polymer strips.

28. The vaginal electrode of claim 27 and further including nonconductive polymer strips separating the conductive polymer strips.

29. A vaginal electrode carrier for supporting a vaginal electrode pad having at least two second conductive fastener sections mounted to the pad and in electrical contact with at least two electrically isolated electrode sections on the electrode pad for contact with a vagina, including:
  an elongated tubular member having an exterior surface and having a plurality of apertures therethrough;
  at least two first conductive fastener sections mounted to the elongated member and communicating with the exterior surface, the first conductive fastener sections cooperable with the second fastener sections of the electrode pad to removably secure the pad to the carrier and couple electrical energy to the electrode sections;
  leads for coupling electrical energy to the first conductive fastener sections.

30. The vaginal electrode carrier of claim 29 wherein the carrier further includes:
  a plurality of sets of first conductive fastener sections; and
  a conductive member coupling the first conductive fastener sections of each set.

31. The vaginal electrode carrier of claim 30 wherein the sets of first conductive fastener sections are arranged circumferentially around the elongated tubular member.

32. The vaginal electrode carrier of claim 30 and further including a fluid resistant polymer coating over the conductive members.

33. The vaginal electrode carrier of claim 29 wherein the apertures are arranged circumferentially around the elongated tubular member and between adjacent sets of first conductive fastener sections.

34. The vaginal electrode carrier of claim 29 wherein the elongated tubular member includes a plastic tubular member.

35. A method of preparing a vaginal electrode for use, the method including:
  providing a carrier for insertion into a vagina, comprising:
    an elongated member having an exterior surface;
    at least two first conductive fastener sections mounted to the elongated member and communicating with the exterior surface; and
    leads for coupling electrical energy to the first conductive fastener sections; and
  wrapping a generally rectangular electrode pad around the carrier, the pad including:
    a flexible pad member conformable to the elongated member and having an outward facing vaginal contact surface and an inward facing carrier contact surface when the pad is wrapped around the carrier
    at least two electrically isolated electrode sections on the vaginal contact surface of the pad member; and
    at least two second conductive fastener sections, each mounted to the pad in electrical contact with one of the electrode sections and communicating with the carrier contact surface; and
  causing the second conductive fastener sections to engage and cooperate with the first fastener sections to removably secure the electrode pad to the carrier and couple electrical energy to the electrode sections.

36. A method of preparing vaginal electrode for use, the method including:
  providing a carrier for insertion into a vagina, comprising:
    an elongated tubular member having a generally circular cross section and an exterior surface;
    a plurality of sets of conductive first snap fastener sections mounted to and arranged about the tubular member and communicating with the exterior surface; and
    leads for coupling electrical energy to the sets of first snap fastener sections; and
  wrapping a generally rectangular electrode pad around the carrier; the pad comprising:
    a flexible pad member conformable to the elongated tubular member and having a vaginal contact surface and a carrier contact surface;
    a plurality of electrode sections arranged on the vaginal contact surface of the pad member so as to be positioned adjacent the sets of first snap fastener sections when the pad member is wrapped around the carrier; and
    a plurality of sets of conductive second snap fastener sections releasably cooperable with the first snap fastener sections; the fastener sections of each set in electrical contact with one of the electrode sections; and.
  causing engagement of the first and second snap fastener sections to removably secure the electrode pad to the carrier and to provide a path for coupling electrical energy to the electrode sections.

37. A vaginal electrode, including:
  a carrier for insertion into a vagina, comprising:
    an elongated plastic tubular member having a generally circular cross section and an exterior surface;
    a plurality of sets of conductive first snap fastener sections mounted to and arranged about the tubular member and communicating with the exterior surface; and
    leads for coupling electrical energy to the sets of first snap fastener sections; and
  an electrode pad removably wrapped around and secured to the carrier; the pad comprising:
    a flexible pad member conformable to the elongated tubular member and having a vaginal contact surface and a carrier contact surface;
    a plurality of electrode sections arranged on the vaginal contact surface of the pad member so as to be positioned adjacent the sets of first snap fastener sections when the pad member is wrapped around the carrier; and
    a plurality of sets of conductive second snap fastener sections releasably cooperable with the first snap fastener sections, the fastener sections of each set in electrical contact with one of the electrode sections; and communicating with the carrier contact surface to removably secure the electrode pad to the carrier and couple electrical energy to the electrode sections.

* * * * *

UNITED STATES PATENT AND TRADEMARK OFFICE
CERTIFICATE OF CORRECTION

PATENT NO. : 5,046,511

DATED : September 10, 1991

INVENTOR(S) : Donald D. Maurer et al.

It is certified that error appears in the above-identified patent and that said Letters Patent is hereby corrected as shown below:

Col. 4, line 48, delete "sections", insert --section--.

Signed and Sealed this

Twenty-second Day of December, 1992

Attest:

DOUGLAS B. COMER

Attesting Officer

Acting Commissioner of Patents and Trademarks